United States Patent
Xiaohai et al.

(10) Patent No.: US 8,329,314 B1
(45) Date of Patent: Dec. 11, 2012

(54) HERMETICALLY BONDING CERAMIC AND TITANIUM WITH A PALLADIUM BRAZE

(75) Inventors: Tom Xiaohai, Simi Valley, CA (US); Michael S Colvin, Malibu, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2355 days.

(21) Appl. No.: 11/238,602

(22) Filed: Sep. 29, 2005

Related U.S. Application Data

(60) Provisional application No. 60/618,077, filed on Oct. 12, 2004.

(51) Int. Cl.
*B32B 15/04* (2006.01)

(52) U.S. Cl. ........ 428/632; 428/621; 428/635; 428/661; 428/670; 428/680; 428/615; 428/640; 228/122.1; 228/124.6; 228/245; 228/246; 228/248.1; 228/262.1; 228/56.3; 623/3.1

(58) Field of Classification Search ........................ None
See application file for complete search history.

(56) References Cited

U.S. PATENT DOCUMENTS

| | | | |
|---|---|---|---|
| 3,594,895 A | 7/1971 | Hill et al. | |
| 3,662,455 A | 5/1972 | Anderson | |
| 3,718,142 A | 2/1973 | Mulier | |
| 3,994,430 A | 11/1976 | Cusano et al. | |
| 4,678,868 A | 7/1987 | Kraska et al. | |
| 4,854,495 A | 8/1989 | Yamamoto et al. | |
| 4,944,861 A * | 7/1990 | Reber | 204/428 |
| 4,991,582 A | 2/1991 | Byers et al. | |
| 5,013,612 A | 5/1991 | Hunt et al. | |
| 5,028,495 A | 7/1991 | Hirano et al. | |
| 5,046,242 A | 9/1991 | Kuzma | |
| 5,193,539 A | 3/1993 | Schulman et al. | |
| 5,193,540 A | 3/1993 | Schulman et al. | |
| 5,272,283 A | 12/1993 | Kuzma | |
| 5,312,439 A | 5/1994 | Loeb | |
| 5,324,316 A | 6/1994 | Schulman et al. | |
| 5,405,367 A | 4/1995 | Schulman et al. | |
| 5,470,345 A | 11/1995 | Hassler et al. | |
| 5,513,793 A | 5/1996 | Malmgren | |
| 5,620,476 A | 4/1997 | Truex et al. | |
| 5,640,764 A | 6/1997 | Strojnik | |
| 5,738,270 A | 4/1998 | Malmgren | |
| 5,750,926 A | 5/1998 | Schulman et al. | |

(Continued)

FOREIGN PATENT DOCUMENTS

JP 58180142 A * 10/1983

(Continued)

OTHER PUBLICATIONS

Semi-Alloys Catalog. Semalloy Brazing Alloys. Jul. 22, 1968.*

(Continued)

*Primary Examiner* — Vera Katz
(74) *Attorney, Agent, or Firm* — Frommer Lawrence & Haug LLP; Bruce E. Black

(57) ABSTRACT

A component assembly for use in living tissue comprises: a ceramic part; a metal part, e.g., a titanium metal; and a palladium (Pd) interlayer for bonding said ceramic part to the metal part. By applying sufficient heat to liquify a palladium-titanium interface, the Pd interlayer is used to braze the ceramic part to the titanium part to yield a hermetic seal.

2 Claims, 5 Drawing Sheets

U.S. PATENT DOCUMENTS

| | | | |
|---|---|---|---|
| 5,782,891 A | 7/1998 | Hassler et al. | |
| 5,811,206 A | 9/1998 | Sunderland et al. | |
| 5,821,011 A | 10/1998 | Taylor et al. | |
| 5,843,140 A | 12/1998 | Strojnik | |
| 5,866,851 A | 2/1999 | Taylor et al. | |
| 5,867,361 A | 2/1999 | Wolf et al. | |
| 5,870,272 A | 2/1999 | Seifried et al. | |
| 5,871,513 A | 2/1999 | Taylor et al. | |
| 6,031,710 A | 2/2000 | Wolf et al. | |
| 6,051,017 A | 4/2000 | Loeb et al. | |
| 6,052,623 A | 4/2000 | Fenner et al. | |
| 6,061,596 A | 5/2000 | Richmond et al. | |
| 6,164,284 A | 12/2000 | Schulman et al. | |
| 6,175,764 B1 | 1/2001 | Loeb et al. | |
| 6,181,965 B1 | 1/2001 | Loeb et al. | |
| 6,185,452 B1 | 2/2001 | Schulman et al. | |
| 6,185,455 B1 | 2/2001 | Loeb et al. | |
| 6,208,894 B1 | 3/2001 | Schulman et al. | |
| 6,214,032 B1 | 4/2001 | Loeb et al. | |
| 6,221,513 B1 | 4/2001 | Lasater | |
| 6,259,937 B1 | 7/2001 | Schulman et al. | |
| 6,284,080 B1 * | 9/2001 | Haq et al. | 156/89.16 |
| 6,315,721 B2 | 11/2001 | Schulman et al. | |
| 6,349,025 B1 | 2/2002 | Fraley et al. | |
| 6,465,327 B1 * | 10/2002 | Aspar et al. | 438/458 |
| 6,516,808 B2 | 2/2003 | Schulman | |
| 6,521,350 B2 | 2/2003 | Fey et al. | |
| 6,553,263 B1 | 4/2003 | Meadows et al. | |
| 6,582,441 B1 | 6/2003 | He et al. | |
| 6,586,675 B1 | 7/2003 | Bealka et al. | |
| 6,607,843 B2 | 8/2003 | Ruth, II et al. | |
| 6,622,046 B2 | 9/2003 | Fraley et al. | |
| 6,660,116 B2 | 12/2003 | Wolf et al. | |
| 6,735,474 B1 | 5/2004 | Loeb et al. | |
| 6,736,770 B2 | 5/2004 | Leysieffer et al. | |
| 6,738,672 B2 | 5/2004 | Schulman et al. | |
| 6,885,895 B1 | 4/2005 | Whitehurst et al. | |
| 6,901,294 B1 | 5/2005 | Whitehurst et al. | |
| 6,901,296 B1 | 5/2005 | Whitehurst et al. | |
| 6,918,530 B2 | 7/2005 | Shinkai et al. | |
| 6,935,897 B2 | 8/2005 | Canfield et al. | |
| 6,941,171 B2 | 9/2005 | Mann et al. | |
| 6,986,453 B2 | 1/2006 | Jiang et al. | |
| 6,989,200 B2 | 1/2006 | Byers et al. | |
| 2003/0096162 A1 | 5/2003 | Lasater et al. | |
| 2004/0058186 A1 | 3/2004 | Daulton | |
| 2004/0059392 A1 | 3/2004 | Parramon et al. | |
| 2004/0136859 A1 * | 7/2004 | Chern Lin et al. | 420/417 |
| 2005/0240229 A1 | 10/2005 | Whitehurst et al. | |

FOREIGN PATENT DOCUMENTS

| | | | |
|---|---|---|---|
| JP | 58180142 A | * 10/1983 | |
| JP | 61082996 A | 4/1986 | |
| JP | 62199288 A | 9/1987 | |
| JP | 3193292 A | 8/1991 | |
| WO | WO0056394 A1 | 9/2000 | |
| WO | WO0056677 A1 | 9/2000 | |
| WO | WO0124962 A1 | 4/2001 | |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Loeb, et al., "BION™ Bionic Neurons for Functional and Therapeutic Electrical Stimulation", 20th Annual International Conference of IEEE Engineering in Medicine and Biology "Biomedical Engineering Towards the Year 2000 and Beyond", Oct. 29-Nov. 1, 1998, Hong Kong, 5 pages.

Loeb, et al., "North Sea: Transducers and Electrodes—Injectable Microstimulator for Functional Electrical Stimulation", Med. & Biol. Eng. & Computer, North Sea Special Feature, (Nov. 29, 1991), pp. NS13-NS19.

U.S. Appl. No. 11/238,603, Official Communication mailed Apr. 28, 2009 (14 pages).

U.S. Appl. No. 11/238,603, Official Communication mailed Sep. 8, 2008 (11 pages).

U.S. Appl. No. 11/238,603, Official Communication mailed Mar. 17, 2008 (10 pages).

* cited by examiner

HERMETICALLY BONDING CERAMIC AND TITANIUM WITH A PALLADIUM BRAZE

The present application claims the benefit of U.S. Provisional Patent Application Ser. No. 60/618,077, filed Oct. 12, 2004, which application is incorporated herein by reference in its entirety.

BACKGROUND OF THE INVENTION

The present disclosure relates to implantable medical devices and, more particularly, systems and methods that permit a titanium or titanium alloy part and a ceramic part to be brazed together to achieve a hermetic seal.

Body implanted devices are generally hermetically sealed to keep fluids and water vapor from infiltrating into the device and destroying the electronic circuitry contained within the device. Typically, the medical device has an outer housing that is made of a biocompatible material such as a ceramic or a metal.

While a medical device housing may be made almost entirely of a biocompatible metal such as titanium, it may be necessary for example, in some medical applications to have a housing which is made substantially from a non-metallic material because a receiving/transmitting antenna may be included inside the housing. Such an antenna may not be operable within a housing that is completely made from metal, e.g., titanium, since metal can effectively act as a shield against RF energy transmissions.

One such application where it is often, for example, to have a composite device housing consisting of a non-metal material, e.g., a ceramic, and a metal, e.g., titanium, is an implantable microstimulator. A microstimulator has very small dimensions and can have metal electrode contacts integrated into the housing. The small dimensions allow a microstimulator to be implanted with less surgical trauma compared to a larger, implantable stimulator device.

Because of the small size of a microstimulator, it generally does not use a primary (one-time-use-only) battery but uses, instead, a replenishable power source such as a rechargeable battery. The rechargeable battery, contained in the microstimulator, is charged inductively with transcutaneous RF power transmissions. In addition, the RF transmissions may also be used to transfer data and commands between the implanted device and the external device that is connected to the secondary antenna. Such RF power/data transmissions require the use of a primary, internal antenna that may be placed inside the device housing and a secondary, external antenna that is not implanted. In order to achieve effective and efficient RF power transmissions through the stimulator housing, the housing can be made at least partly of a non-metallic material. The use of a housing that is at least partly non-metallic can improve the magnetic inductance between the internal antenna within or on the implantable device and an external antenna.

An example microstimulator that employs a rechargeable battery and derives power from transcutaneous RF power transmissions is a BION® implantable microstimulator, manufactured by Advanced Bionics® Corporation, Valencia, Calif.

The following list of applications, publications and patents, which are all herein incorporated by reference, describe various details associated with the manufacture, operation and use of BION implantable microstimulators.

| Application/<br>Patent/<br>Publication No. | Filing/<br>Publication<br>Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
|  | Published September, 1997 | Micromodular Implants to Provide Electrical Stimulation of Paralyzed Muscles and Limbs, by Cameron, et al., published in IEEE Transactions on Biomedical Engineering, Vol. 44, No. 9, pages 781-790. |

The BION microstimulator has a small housing that may be partly metal, e.g., titanium and partly non-metallic, e.g., a ceramic. Because the microstimulator uses a rechargeable battery and contains an antenna for receiving power and/or data transmissions, it may be necessary for example, for at least a part of the housing to be non-metallic. In addition, because the microstimulator has both anode and cathode electrode contacts, which are typically both metals, it may be necessary for example, to hermetically seal the interface between the metal electrode contacts and the non-metallic, e.g., ceramic part of the housing. Thus, the housing may comprise a metal part and a non-metallic part, which two parts exhibit different mechanical properties. The construction of such a composite housing for a microstimulator is challenging because: (1) the two dissimilar materials, ceramic and titanium have different mechanical properties, including thermal coefficients of expansions and (2) the method of joining for example, must yield a strong, hermetic seal.

Nickel has been used to create a brazed interface. U.S. Pat. No. 6,521,350 to Fey et al. employs an interlayer of pure nickel to form a bond between a ceramic part and a titanium part. U.S. Pat. No. 6,221,513 to Lasater uses a titanium nickel (Ti—Ni) alloy as interface material between ceramic and titanium. Both patents are herein incorporated by reference in their entireties.

A need exists for alternative systems and methods for hermetically sealing a medical device housing that may be partly ceramic and partly titanium.

SUMMARY OF THE INVENTION

A component assembly provides a hermetic seal between a titanium part and a ceramic part, which component assembly is implantable within living tissue, e.g., a human body. A palladium interface layer (interlayer), e.g., in a sheet or foil form, can be placed between the titanium part and ceramic part and pressed together to get intimate contact between all parts. While the complete assembly is placed in an inert gas, e.g., argon, or in a vacuum, heat is applied until a temperature is reached, where the Pd interface melts. After cooling, the palladium forms a eutectic bond with the titanium part and also wets the ceramic surface and forms a bond with the ceramic after the palladium interlayer is allowed to cool. The resulting brazed interface is strong and provides a hermetic seal that is essentially impervious to the passage of gases or water.

In a particular embodiment utilizing the hermetic component assembly, an implantable microstimulator housing employs a titanium part and a ceramic part and an interface layer (interlayer) of palladium (Pd). The microstimulator housing is hollow and the space inside can be filled with components, e.g., a rechargeable battery and associated stimulation electronics.

BRIEF DESCRIPTION OF THE DRAWINGS

The above and other aspects of the present disclosure will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
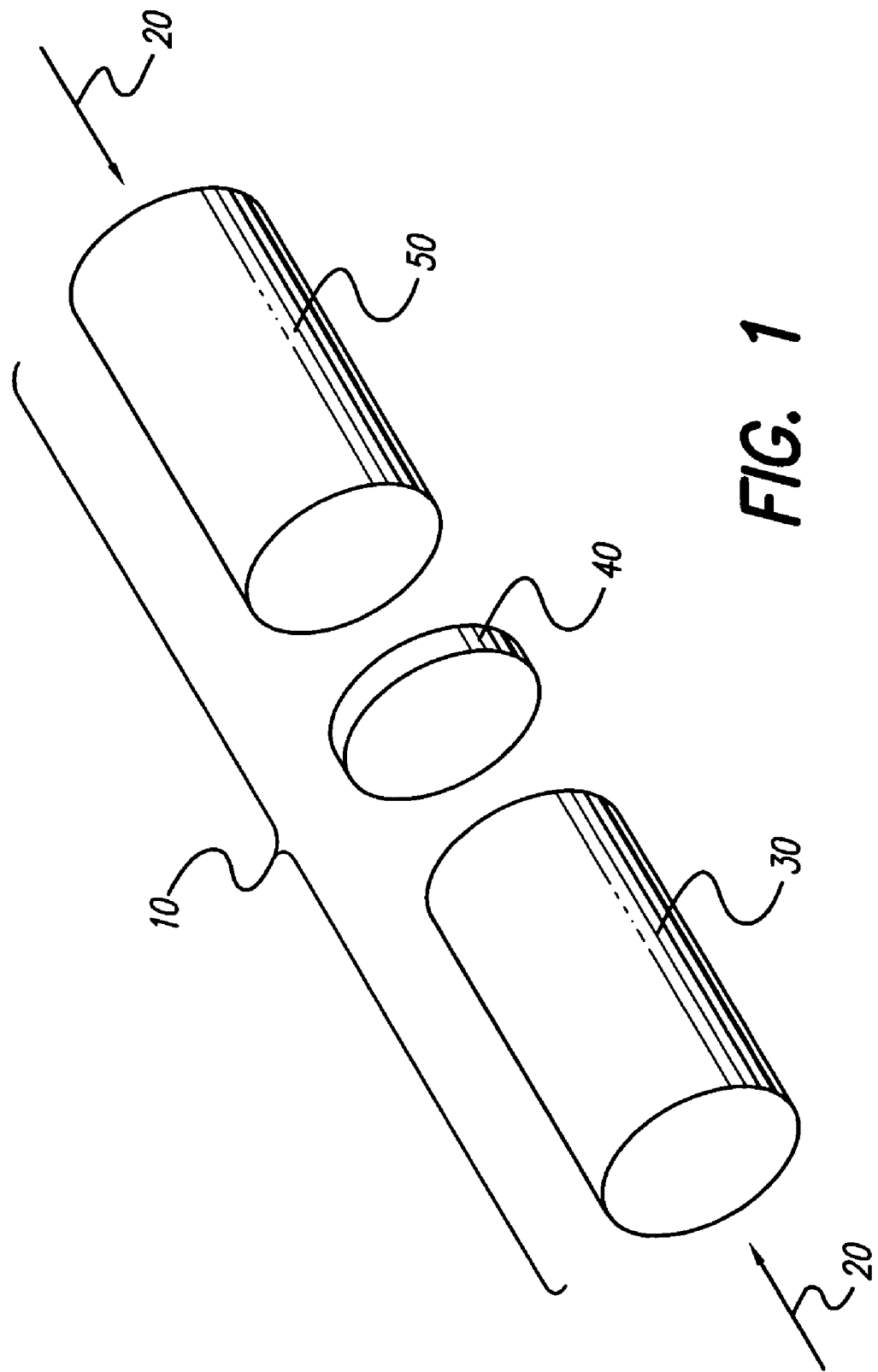
FIG. 1 shows an illustration of a system for hermetically sealing an interface between a ceramic component and a titanium component.

FIG. 1 shows a view of a component assembly system 10 for achieving a hermetic seal between a titanium part 30 and a ceramic part 50, which system may be implanted in living tissue. The assembly system includes a palladium (Pd) interface layer (interlayer) 40 placed between the titanium part 30 and ceramic part 50.

Figure 2:
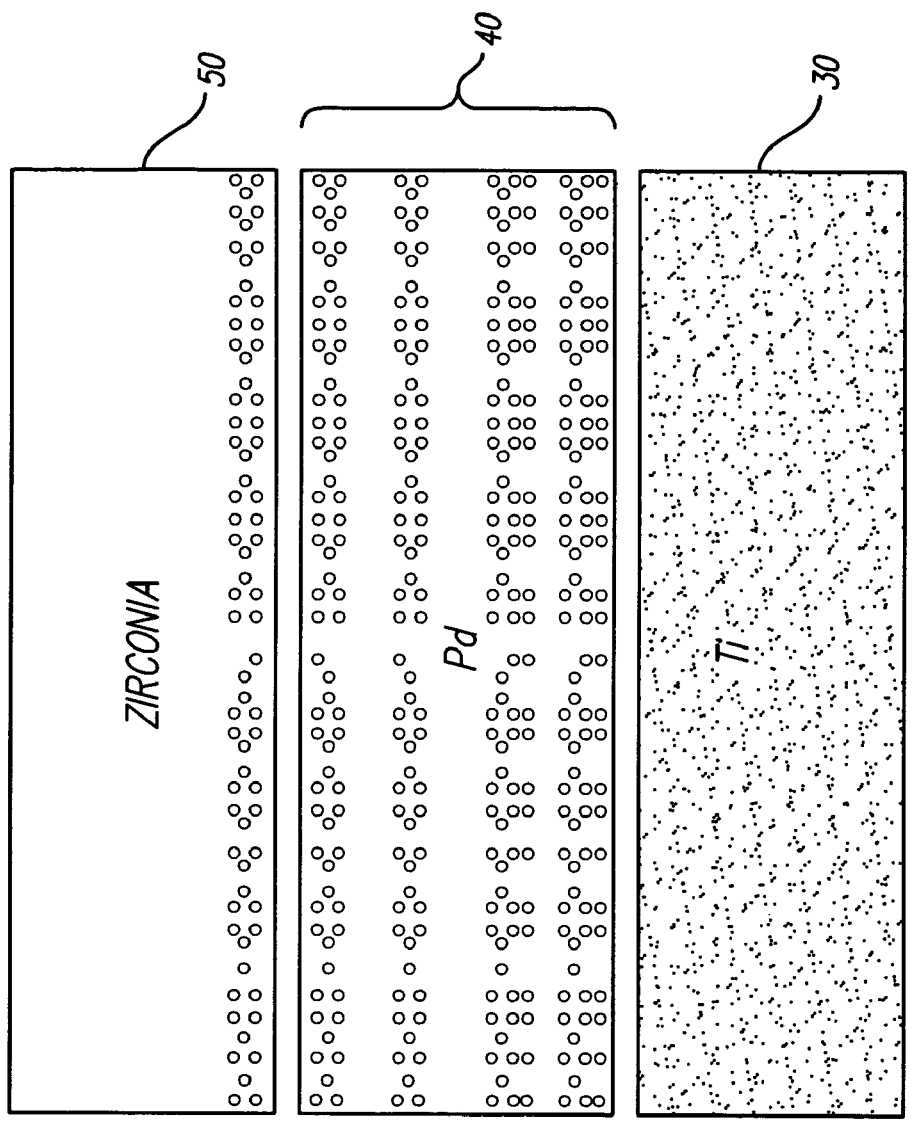
FIG. 2 shows a representation of a ceramic part, e.g., zirconia, and titanium or titanium alloy part with a Pd interlayer.

FIG. 2 shows a cross-section of a Pd interlayer 40. FIG. 2 also shows the component parts of the hermetic assembly: a ceramic 50, e.g., a zirconia ceramic part, a titanium part 30 and the Pd interlayer 40. In one of many possible examples, the laminate interlayer 40 is cold rolled into a single-layer foil. The titanium part 30 may be a commercially pure titanium or a titanium alloy, including among others, Ti-6 Al-4 V, titanium niobium alloy or titanium tantalum. The ceramic part 50 may be, among others, zirconia, stabilized zirconia, partially stabilized zirconia, tetragonal zirconia, magnesia stabilized zirconia, ceria-stabilized zirconia, yttria stabilized zirconia, and calcia stabilized zirconia, as well as alumina, titania, and the like To achieve a hermetic seal, the interlayer 40 can be placed between the titanium part 30 and ceramic part 50 and pressure (force) of between 5 to 20 psi may be applied to urge the titanium part 30 and ceramic part 50 to firmly press against the laminate interlayer 40. While pressure is applied to achieve good material contact, the titanium part 30, the ceramic part 50 and laminate interlayer 40 are placed in a vacuum, e.g., at about $10^{-6}$ torr or in a non-reactive gas, such as argon, and then the parts are heated to a temperature at or above the Ti—Pd eutectic temperature, e.g., 1120 degrees C., that causes the palladium interlayer 40 and titanium part 30 to fuse together and cause wetting of the surface of the ceramic part 50. The melting temperature of the Pd interlayer 40 adjacent to the titanium part 30, for example, is lower than a melting temperature for the titanium part 30 by itself or the melting temperature for the ceramic part 50.

Figure 3:
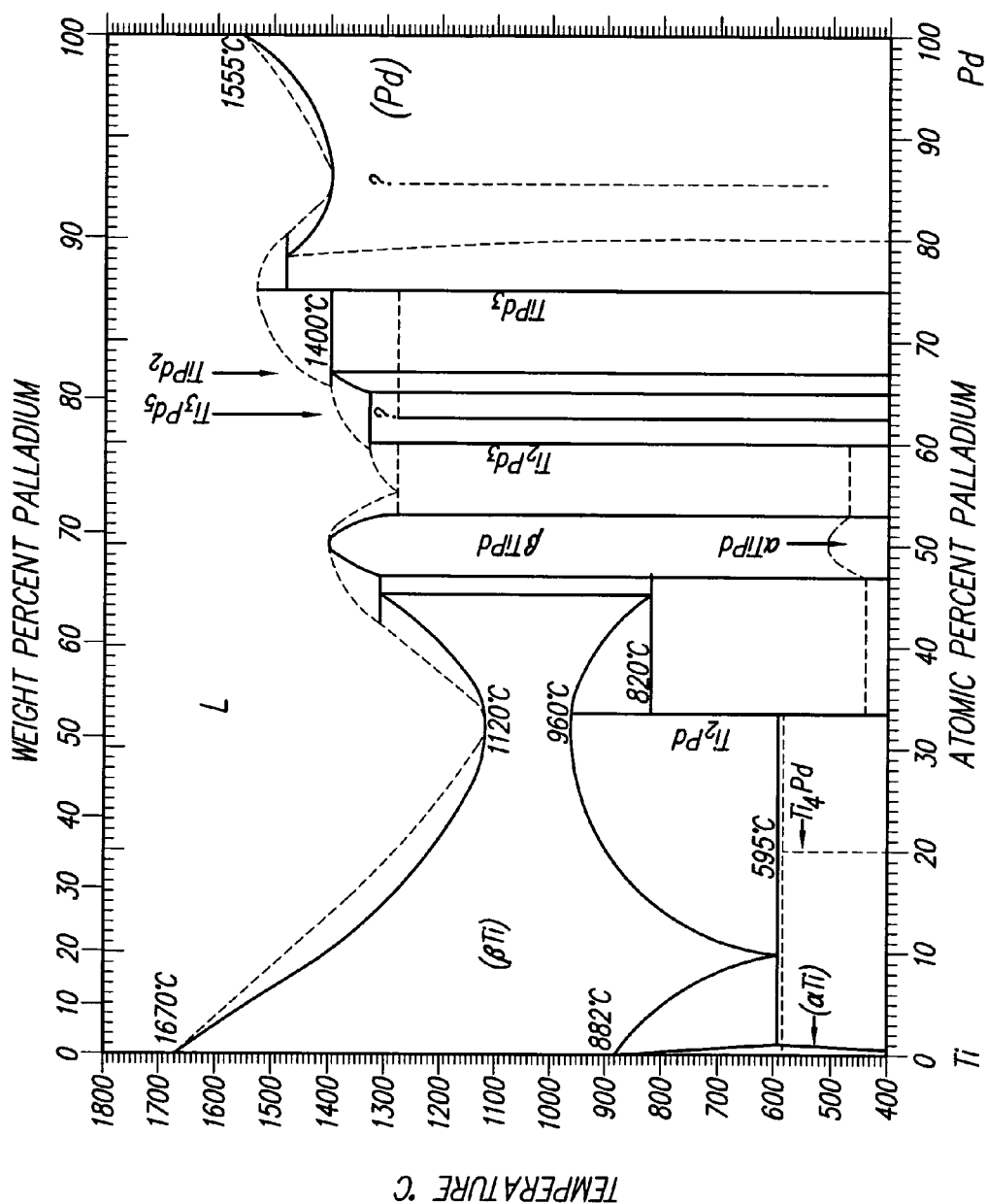
FIG. 3 shows a solid-liquid phase diagram for titanium-palladium.

FIG. 3 shows a liquid-solid phase diagram for titanium-palladium (Ti—Pd). This diagram indicates an X-axis (shown at the bottom of the graph) of atomic percent of palladium relative to titanium or, alternatively, weight percent of palladium relative to titanium (shown at the top of the graph). The Y-axis indicates the temperature in degrees Celsius. The dotted line at the upper area of the graph demarcates the upper area labeled "L", which dotted line indicates the temperatures and percentage weights of palladium wherein the palladium/titanium interlayer will begin to liquify. Below the dotted line at the upper part of the graph, the palladium/titanium is in the solid phase. It can be seen that at a 50% weight of palladium relative to titanium/palladium, the Ti—Pd will enter a liquid phase at a temperature at or above 1120 degrees C. At some melting temperature, the Pd—Ti interface between the palladium interlayer 40 and the titanium part 30 will be in a liquid state and conform to the surface of the ceramic part 50 (FIG. 2). As the titanium-palladium interface 40 cools, a bond forms between the ceramic part 50 and the Pd interlayer 40. In addition, after cooling, the Pd interlayer 40 will also bond with titanium part 30.

Figure 4:
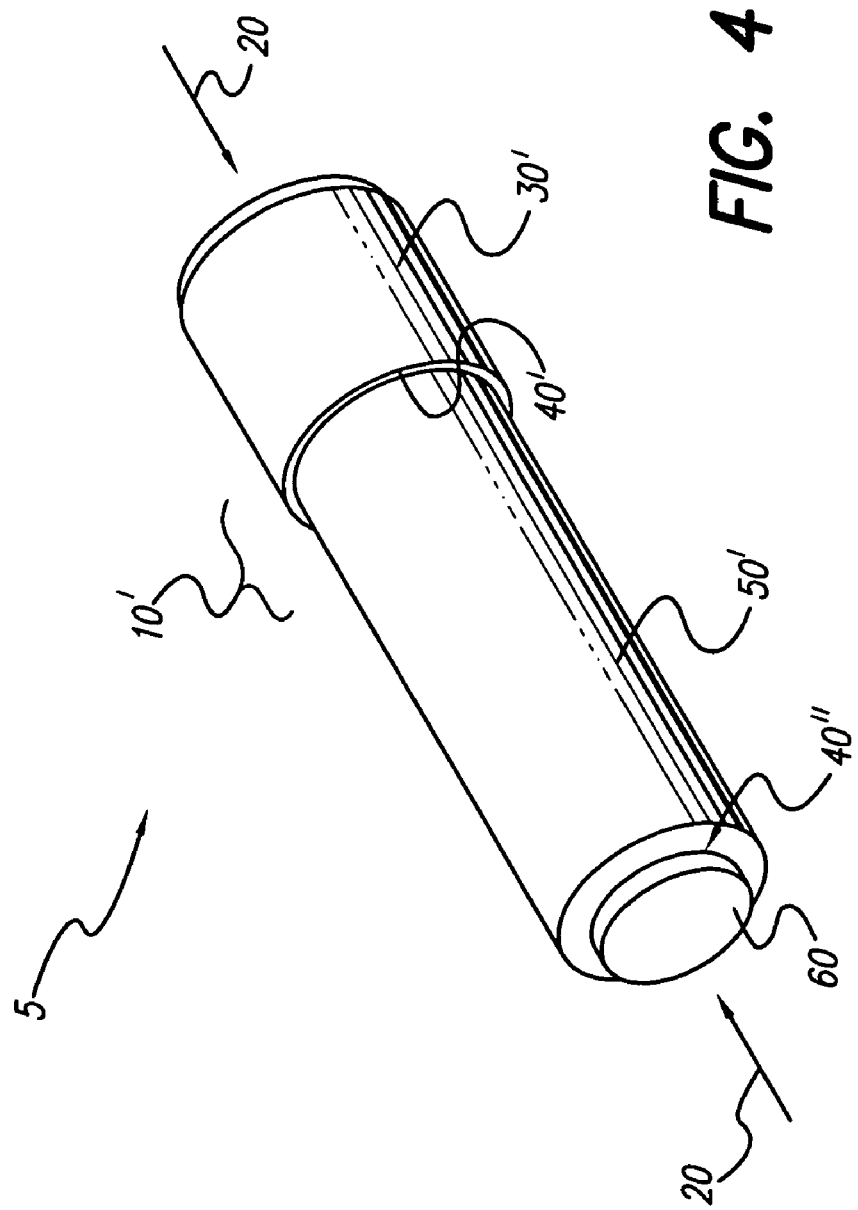
FIG. 4 shows an illustration of a microstimulator having a ceramic part and a titanium part and a palladium interlayer therebetween.

FIG. 4 shows a perspective, external view of a microstimulator housing 5 showing its various parts, which microstimulator housing 5 may have a ceramic part 50', a titanium part 30' and a palladium interlayer 40' therebetween. The three part housing assembly comprising the ceramic part 50', palladium interlayer 40' and the titanium part 30' make up the total component assembly 10' needed to achieve a hermetic seal. The microstimulator housing 5, as shown, also has an electrode contact 60 and may have another interlayer 40" which can also be a Pd braze. Pressure (force) as shown by the arrows 20A and 20B may be applied from both ends of the microstimulator housing to provide intimate contact between component materials during brazing of the palladium to the titanium part 30' and the ceramic part 50'. The pressures (force), as shown by the arrows 20A and 20B, applied to the component materials may be, for example, between 5 to 20 psi. In one embodiment, the interlayer 40' may be placed into a vacuum that is about $10^{-6}$ torr while the Pd brazing occurs.

Figure 5:
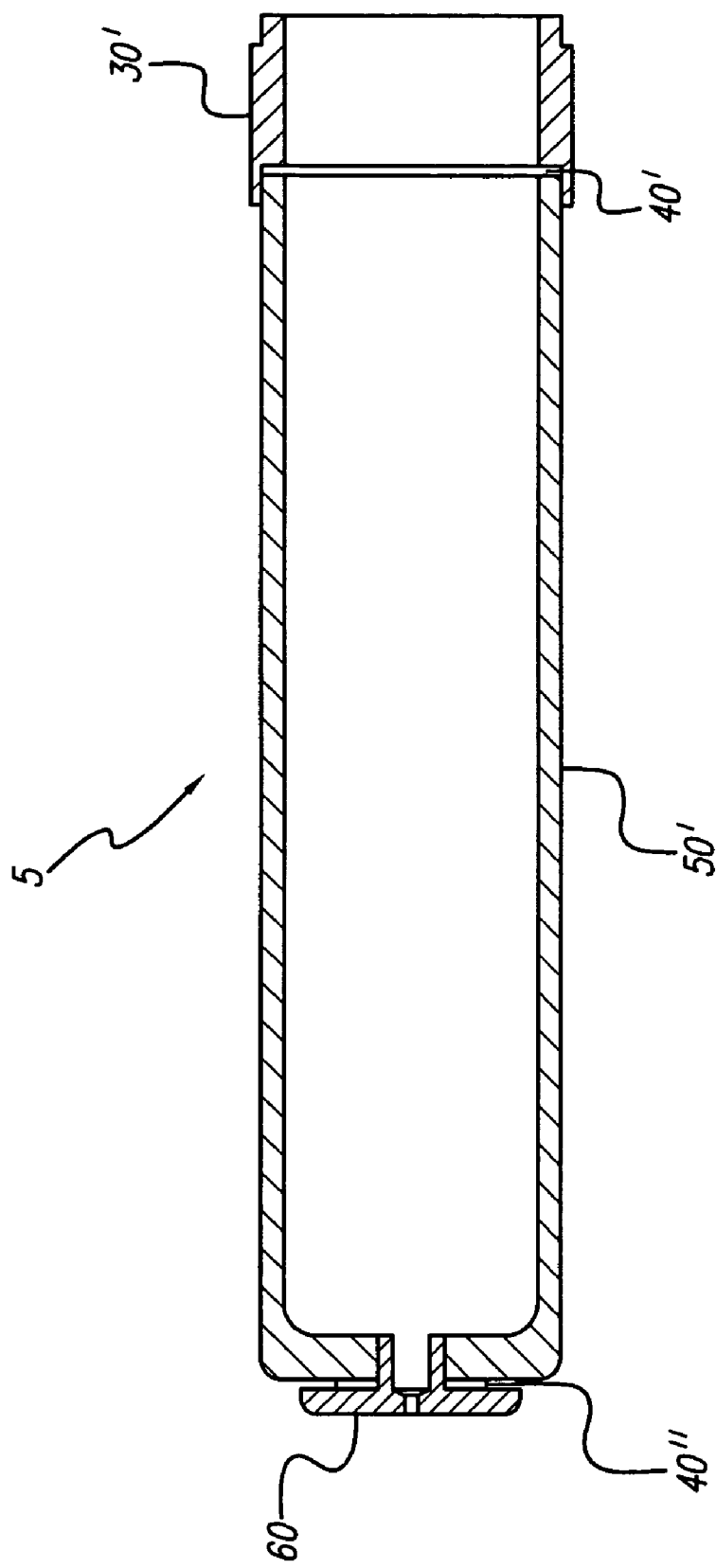
FIG. 5 shows a cross-sectional view of a microstimulator housing ceramic part and a titanium part or titanium alloy part.

FIG. 5 shows a cross-sectional view of a microstimulator housing 5 of FIG. 4. The microstimulator housing 5 is hollow inside and contains internal electronics and parts, e.g., a rechargeable battery (not shown) and electronic circuitry (not shown) for producing electrical stimulation pulses from the electrode contact 60 and titanium part 30', which may function as an electrode. The length of the microstimulator housing 5, may be for example, less than about 1.5 inches and in some examples, may be less than about 1 inch. The diameter of the microstimulator may be less than about 1.5 inches and in some examples, less than about a quarter inch. The electrode contact 60 and titanium part 30' are connected in a circuit. To achieve a hermetic seal, the interface between the ceramic part 50' and titanium part 30' is brazed with an interlayer of palladium 40'. For example, a Pd laminate interlayer 40' may have a total thickness of between about 0.0001 to about 0.01 inches. A thickness of about 0.003 inches, for instance, may be a thickness for use with a microstimulator. It is understood that these dimensions for the Pd interlayer 40' are exemplary only for a particular microstimulator and may vary according to the particular application and size of the medical device.

In sum, to create a hermetic seal for an implantable housing, the Pd brazing steps include: providing a ceramic part and a titanium part, placing a Pd thin foil or a sheet between the ceramic and titanium parts, which parts are held together intimately under a pressure (force) in a vacuum or inert gas environment. In this environment, the titanium part and the Pd interlayer are heated to a temperature exceeding the liquid phase of the Ti—Pd interface, e.g., about 1120 to 1150 degrees Celsius, in order to liquify the Ti—Pd interface and to create a bond between the palladium and the Ti part and between the palladium and the ceramic part.

In may also be possible to provide a Pd interlayer in forms other than a foil or sheet. For example, a mixed powdered form or micro-bead form can also suffice. Certain applications may require the foil to be circular or annular in form to seal a cylindrical, annular surface, or similar surface.

Compared to a nickel braze, for example, it is known that palladium is more inert in the body environment and thus more bio-compatible, i.e., relatively non-reactive within the human body. The bond created between palladium and ceramic is strong and hermetic and is essentially impervious to the passage of gases or water at the brazed interface. The bond created between the palladium interlayer with a commercially pure titanium part or titanium alloy part is also strong and hermetic.

While the invention herein disclosed has been described by means of specific embodiments and applications thereof, numerous modifications and variations could be made thereto by those skilled in the art without departing from the scope of the invention set forth in the claims.

What is claimed is:

1. A microstimulator comprising: a component assembly housing comprising:

a ceramic part; a metal part selected from the group consisting of titanium and titanium alloys; and a palladium (Pd) interface layer consisting of palladium that is combined with a portion of one or both of the metal part or the ceramic part to form a bond between said ceramic part and the metal part, and further comprising an electrode contact and a second palladium interface layer consisting of palladium, wherein the second interface layer bonds the electrode contact to the ceramic part of the component assembly housing.

2. The microstimulator of claim 1, wherein the electrode contact and the metal part of the housing are electrically connected.

\* \* \* \* \*